US00PP35729P2

(12) United States Plant Patent
Rosas et al.

(10) Patent No.: US PP35,729 P2
(45) Date of Patent: Apr. 9, 2024

(54) STRAWBERRY PLANT NAMED 'PLARED 18009'

(50) Latin Name: ***Fragaria* x *ananassa***
Varietal Denomination: Plared 18009

(71) Applicant: Plantas de Navarra, S.A. Sociedad Unipersonal, Valtierra (ES)

(72) Inventors: Manuel Rosas, Valtierra (ES); Craig Stewart Gaines, Valtierra (ES)

(73) Assignee: Plantas de Navarra, S.A. Sociedad Unipersonal, Navarra (ES)

( * ) Notice: Subject to any disclaimer, the term of this patent is extended or adjusted under 35 U.S.C. 154(b) by 0 days.

(21) Appl. No.: 18/134,214

(22) Filed: Apr. 13, 2023

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

*Primary Examiner* — Susan McCormick Ewoldt
(74) *Attorney, Agent, or Firm* — Knobbe, Martens, Olson & Bear, LLP

(57) ABSTRACT

A new and distinct variety of strawberry 'Plared 18009'. The new variety is characterized by high production, compact plant size, low fruiting field runner production, and high resistance to *Fusarium oxysporum*. The new variety is adapted for fall planting for sustained production. The new variety 'Plared 18009' is a day-neutral plant with a semi-upright growth habit.

26 Drawing Sheets

Botanical classification: *Fragaria* x *ananassa*.

Variety denomination: The new variety has the varietal denomination 'Plared 18009'.

BACKGROUND AND SUMMARY OF THE INVENTION

This application relates to the discovery and asexual propagation of a new and distinct variety of strawberry, 'Plared 18009', as herein described and illustrated. The new variety 'Plared 18009' is characterized by high production, low field runner production, semi-upright growth habit, and high resistance to *Fusarium oxysporum*. It is adapted for fall planting and is optimized for sustained production for the fresh fruit market. The new variety 'Plared 18009' is a day-neutral plant with a compact plant size.

The observed characteristics are believed to apply to plants grown under similar conditions of soil and climate elsewhere.

The variety was originated by directed cross between two advanced selections. The seed parent is the varietal selection '16-69R' and the pollen parent is the varietal selection '15-221R'. The parent varieties were first crossed in January 2018. The date of first flowering was July 2018, and the initial growing period was April 2018-January 2019. The new variety was first selected as breeder number '18-009R' in Watsonville, California in between July and October 2018.

The new variety 'Plared 18009' was first asexually propagated from July 2018 to January 2019 in Watsonville, California, by using clonal propagation via stolons. Plants of the new variety 'Plared 18009' were grown by harvesting fresh plants from Macdoel, California in late October that were later planted in Watsonville, California in early November. Internal trials were conducted on 48" raised beds with two rows of plants per bed and 16" of space between plants. Raised beds were prepared using 800 pounds per acre of slow-release fertilizer. Pesticides were applied in anticipation or in response to disease pressure, and soluble fertilizers were applied to maximize fruit production and fruit quality while maintaining optimal plant balance.

COMPARISON TO THE PARENTS

The new variety 'Plared 18009' is distinguished from its seed parent '16-69R' (unpatented) in that the new variety has moderate day-neutrality and medium gauge stems, compared to the strong day-neutrality and thick stems of '16-69R'. Additionally, the new variety 'Plared 18009' produces few stolons in fruiting fields and is adapted for fall planting. In contrast, '16-69R' produces many stolons in fruiting fields and is adapted for summer planting with frozen (frigo) plants.

The new variety 'Plared 18009' is distinguished from its pollen parent '15-221R' (unpatented) in that the new variety has a compact plant size and Light Green 142A colored leaves, compared to a to large plant size and Dark Green 134A colored leaves for '15-221R'. Further, the fruit of the new variety 'Plared 18009' is Light Red Medium Orange-Red 34A in color and the variety is adapted for sustained production, compared a Dark Red 45B colored fruit of '15-221R', which is adapted for early production.

COMPARISON TO CLOSEST VARIETY

The new variety 'Plared 18009' is distinguished from all currently available strawberry varieties by its combination of a compact plant size, low fruiting field runner production and high resistance to *Fusarium oxysporum*. The new variety 'Plared 18009' has shorter petioles than 'Monterey' resulting in a more compact plant which is easier to harvest. 'Plared 18009' has been observed to produce fewer fruiting field runners than 'Monterey' (U.S. Plant Pat. No. 19,767);

in this regard it is more like the variety 'San Andreas' (U.S. Plant Pat. No. 19,975). 'Plared 18009' has been trialed in *Fusarium* infested fields and been observed to be highly resistant, while 'Monterey' is widely known to be susceptible.

Additionally, 'Plared 18009' is highly productive. During the 2021-2022 Fall planted internal trials in Watsonville, California, 'Plared 18009' produced 2891.0 grams of marketable fruit per plant (standard error 91.2 grams), while 'Monterey' produced 2093.9 grams of marketable fruit per plant (standard error 53.5 grams). Between the Fall planted 2019-2020 and 2020-2021 internal trials in Watsonville, California, 'Plared 18009' produced 22.3% more marketable fruit than 'Monterey'.

TABLE 1

TABLE 1 shows a comparison between the new variety 'Plared 18009' and 'Monterey'. 2021-2022 INTERNAL FALL PLANTING TRIAL

| | 'Monterey' | 'Plared 18009' |
|---|---|---|
| Total Marketable Yield (GR/PL) | 2093.9 | 2891.0 |
| % Cull | 19% | 19.3% |
| Average Individual Fruit Weight (GR/FR) | 27.6 | 27.7 |
| Average % Brix | 10.2 | 8.8 |
| Average Firmness (GR/1.25 cm2) | 884.7 | 863.9 |
| Average Post-Harvest (1-5 score) | 3.2 | 3.3 |

**Average Post Harvest refers to a qualitative breeder's score of fruit appearance given after a week of post-harvest storage. The breeder's score is on a scale of 1 to 5. When giving the score the breeder considers fruit bruising, presence of mold, calyx freshness, fruit sheen, and fruit color.

BRIEF DESCRIPTION OF PHOTOGRAPHS

The accompanying photographs show typical specimens of the new variety 'Plared 18009', including fruit, foliage, and flower, in color as nearly true as it is reasonably possible to make in color illustrations of this character.

The plants depicted in the photographs were planted Nov. 11, 2021 in Watsonville, California. The photographs were taken Aug. 31, 2022 when there was a minimum temperature of about 52° F. and a maximum temperature of about 65° F.

Figure 1:
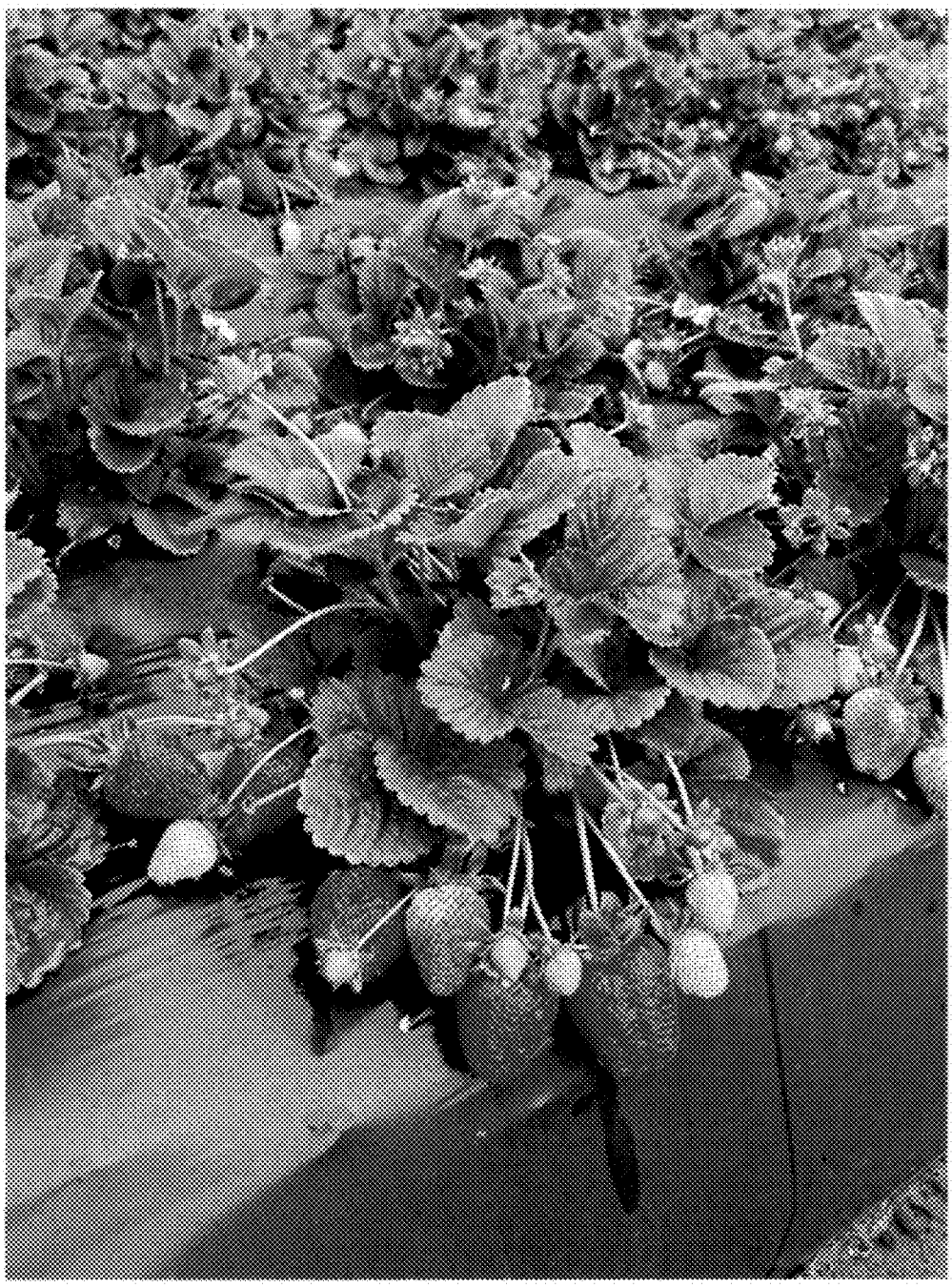
FIG. 1 and FIG. 2 show several plants of the new variety having several Medium Orange-Red 34A colored and conical shaped fruits.
Figure 2:
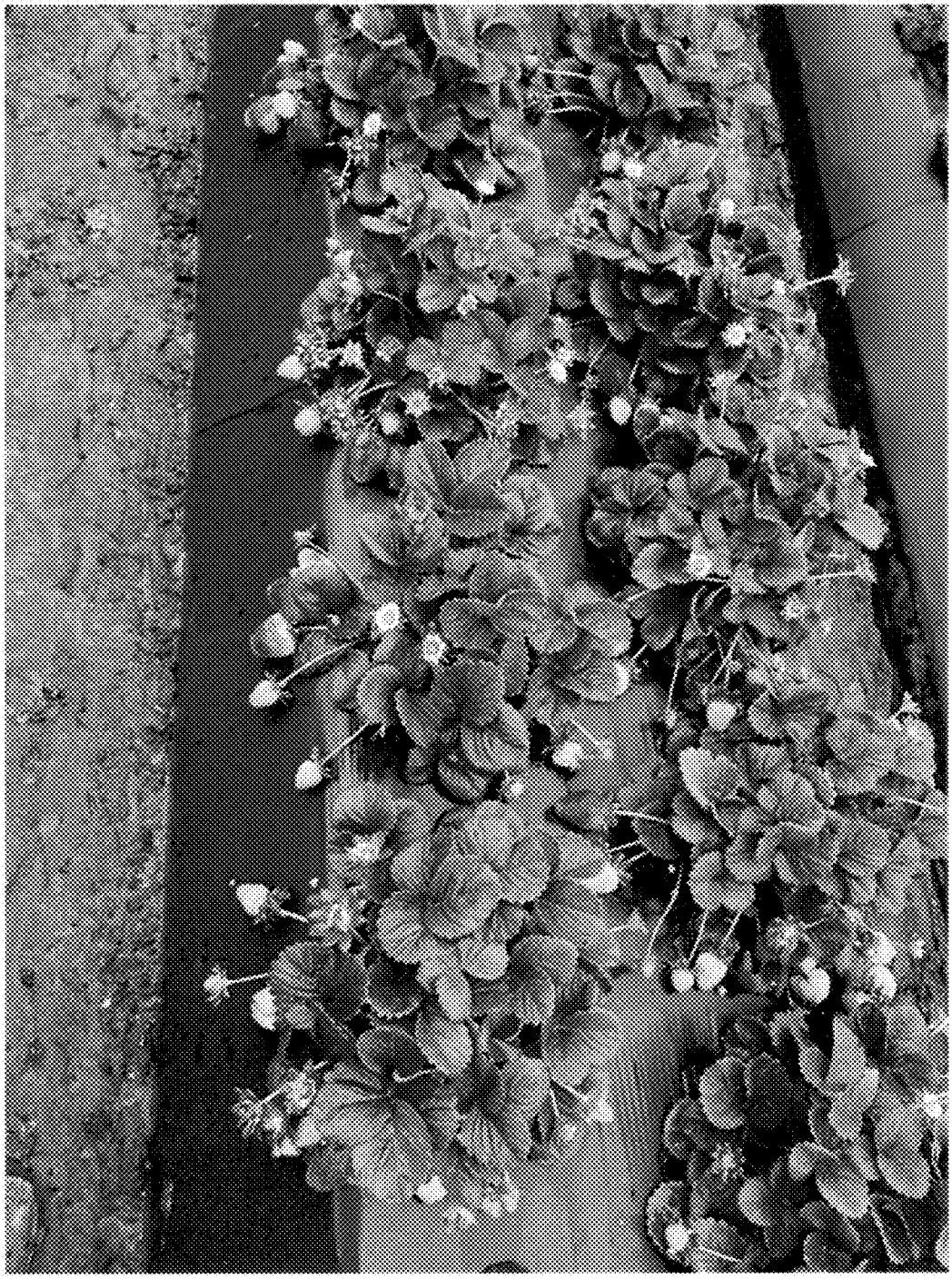
Figure 3:
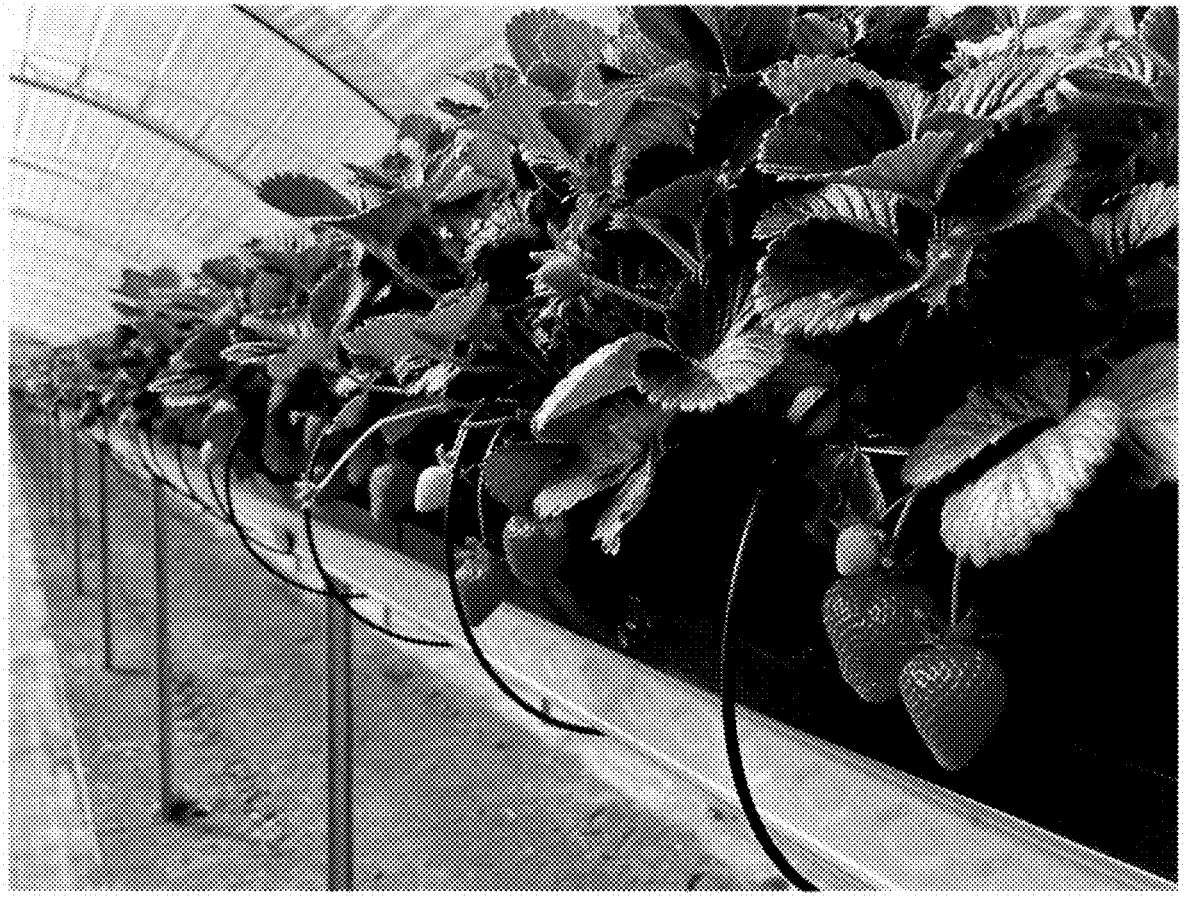
FIG. 3 shows several plants of the new variety 'Plared 18009' that exhibit a semi-upright habit, a medium density compared to 'Montery' and the position of the inflorescence slightly above the foliage.
Figure 4:
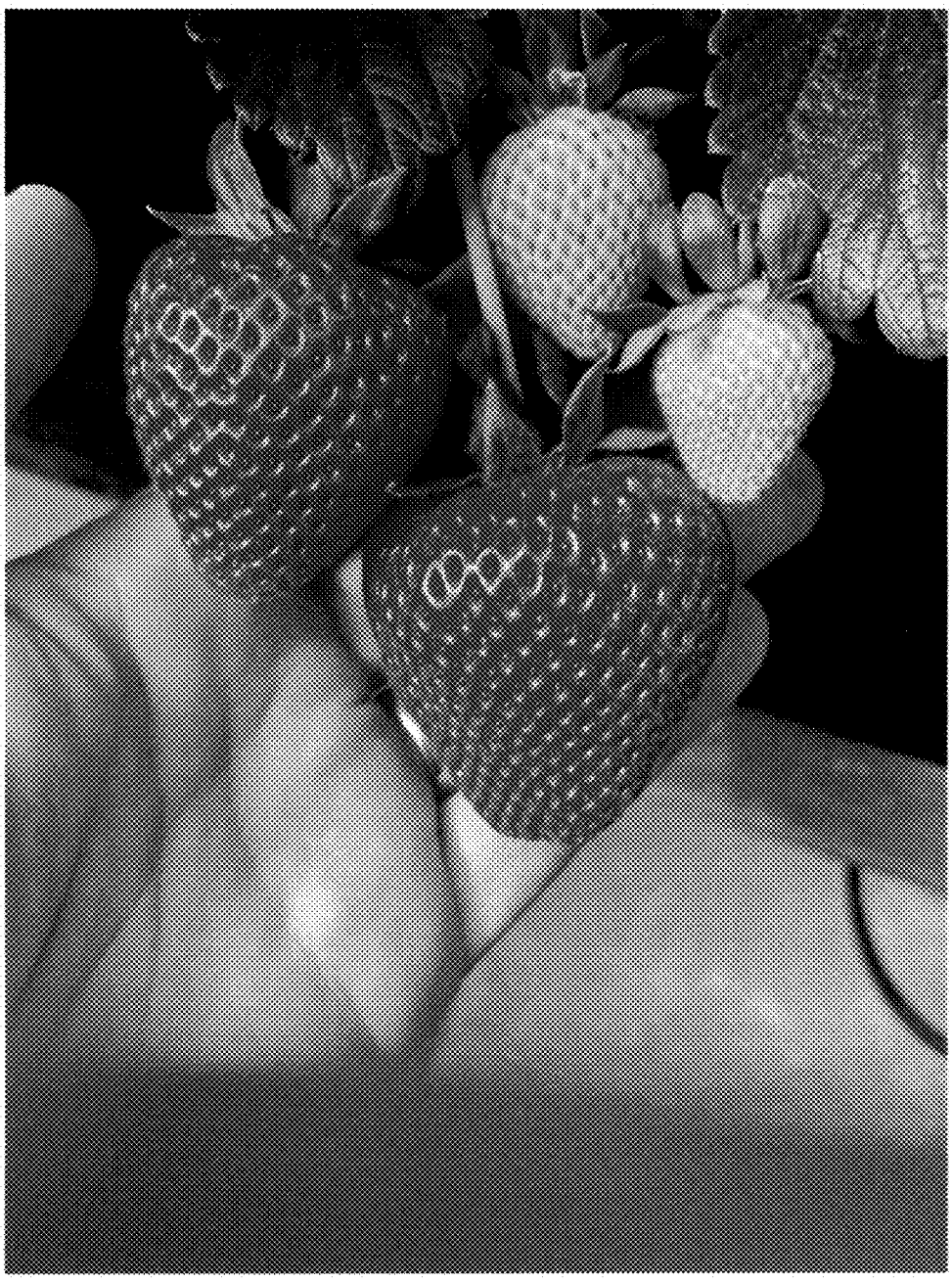
FIG. 4 show the Medium Orange-Red 34A colored fruit of the new variety 'Plared 18009'.
Figure 5:
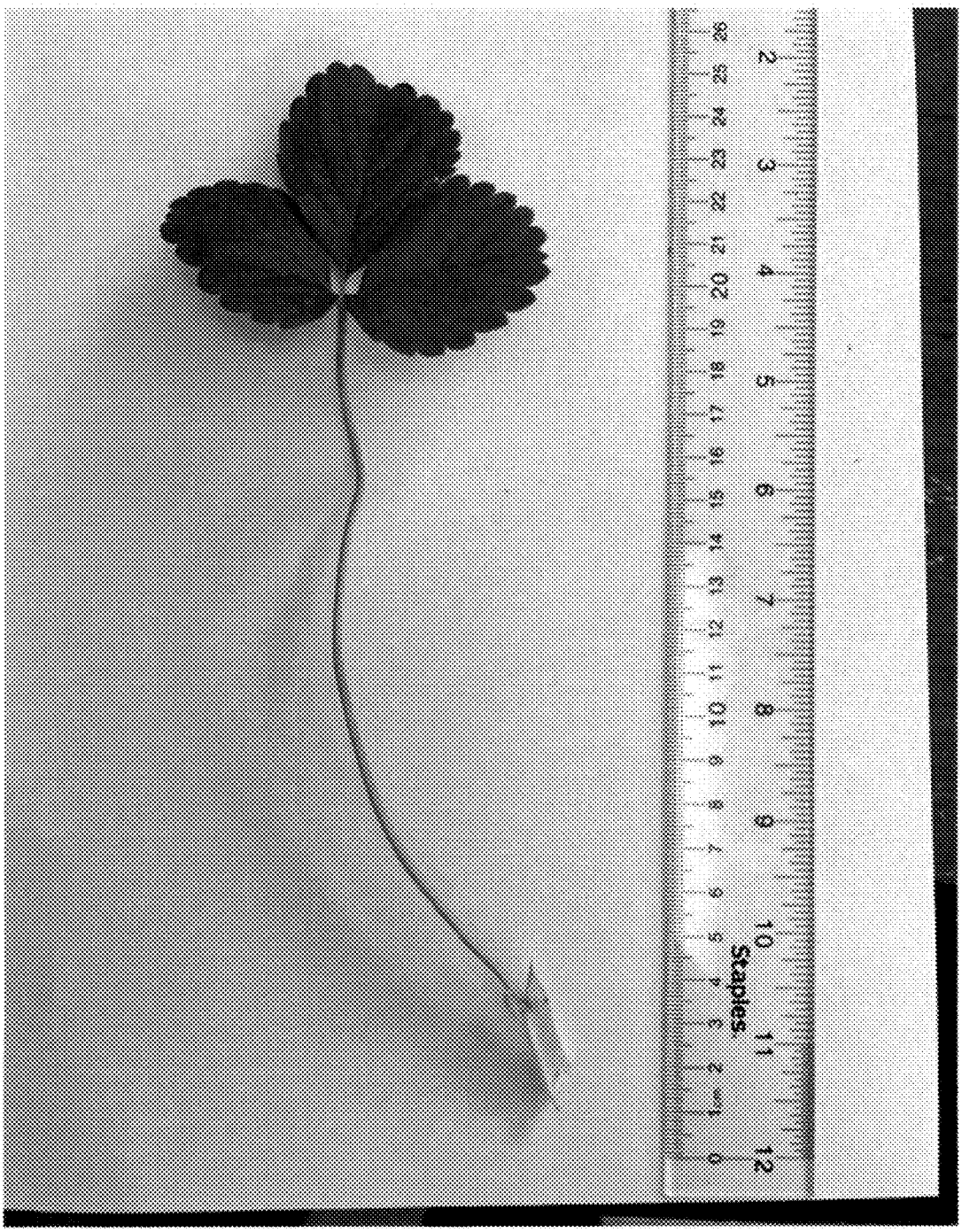
FIG. 5 shows the upper side of a complete leaf of the new variety 'Plared 18009'.
Figure 6:
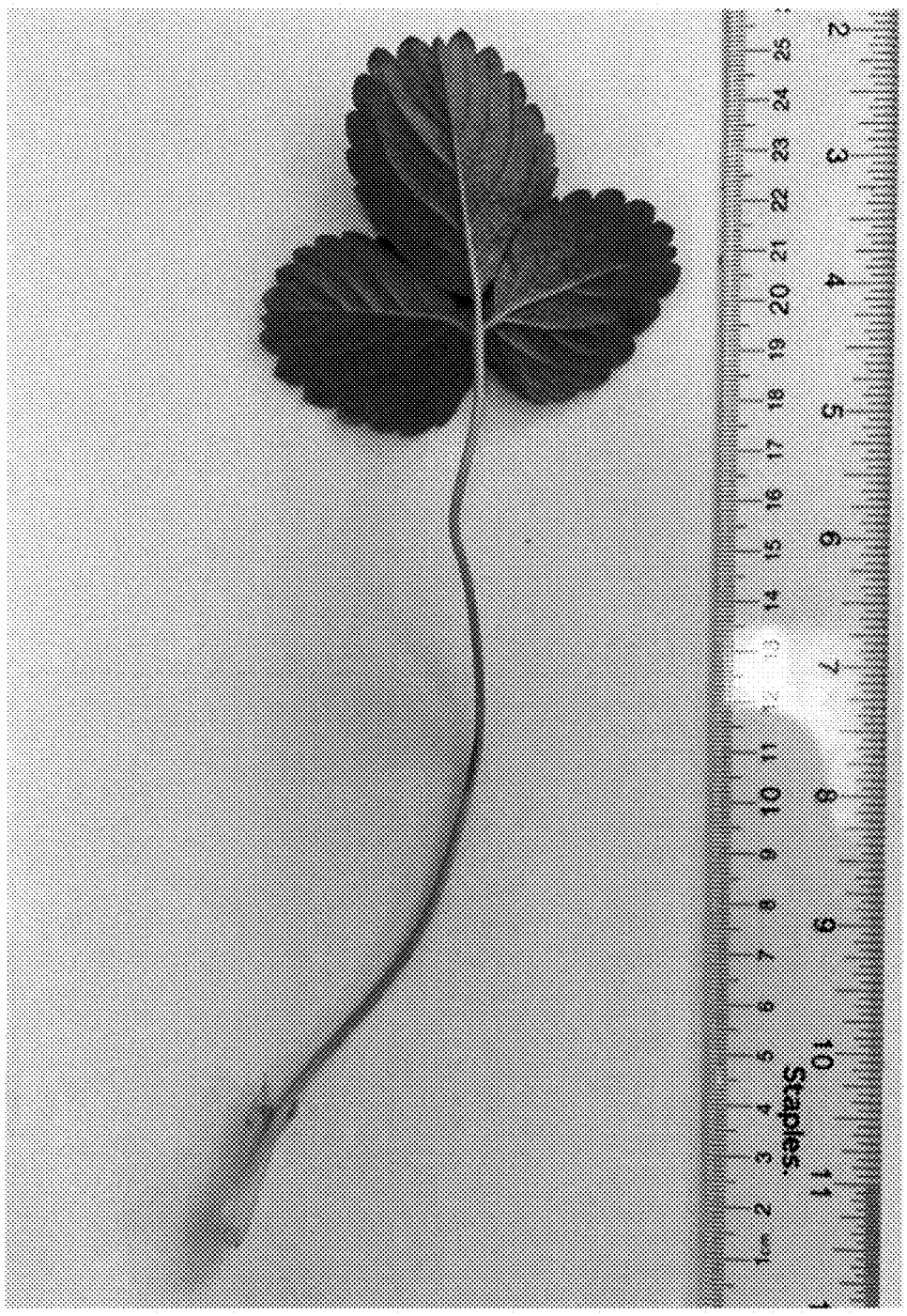
FIG. 6 shows the underside of a complete leaf of the new variety 'Plared 18009'.
Figure 7:
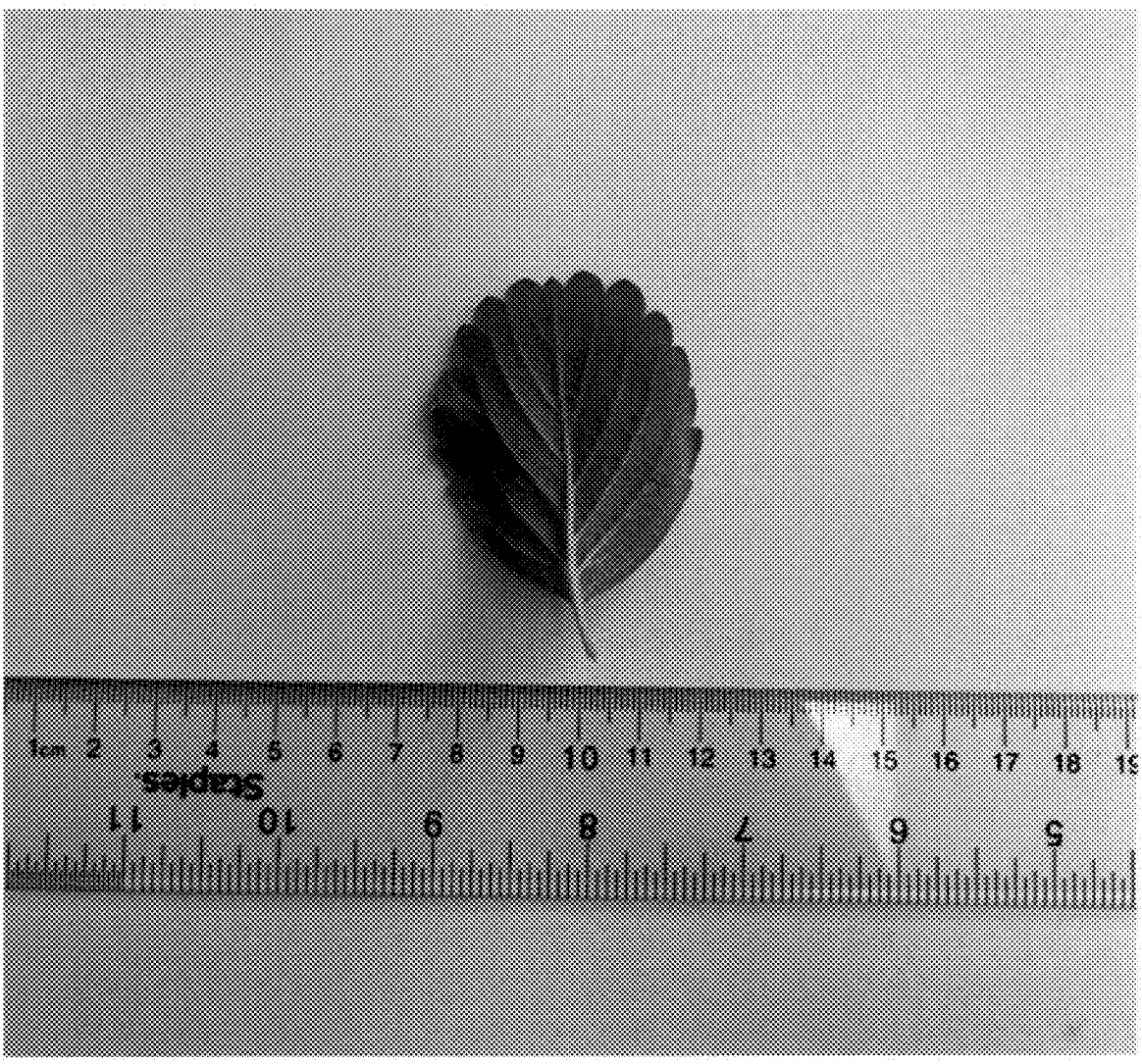
FIG. 7 shows the underside and FIG. 8 shows the upper side of the terminal leaflet of the new variety 'Plared 18009'. The concave shape of the base can be observed.
Figure 8:
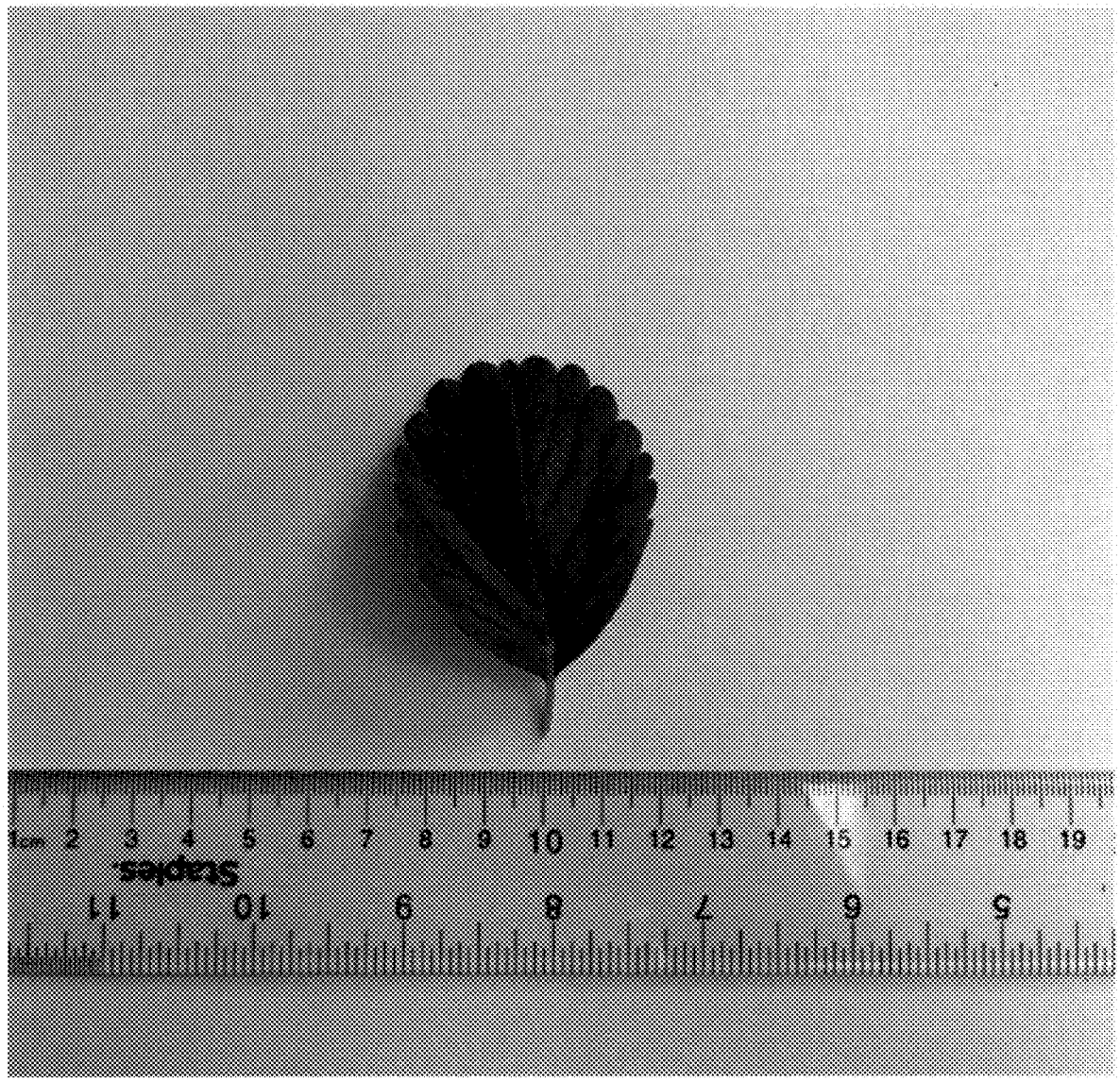
Figure 9:
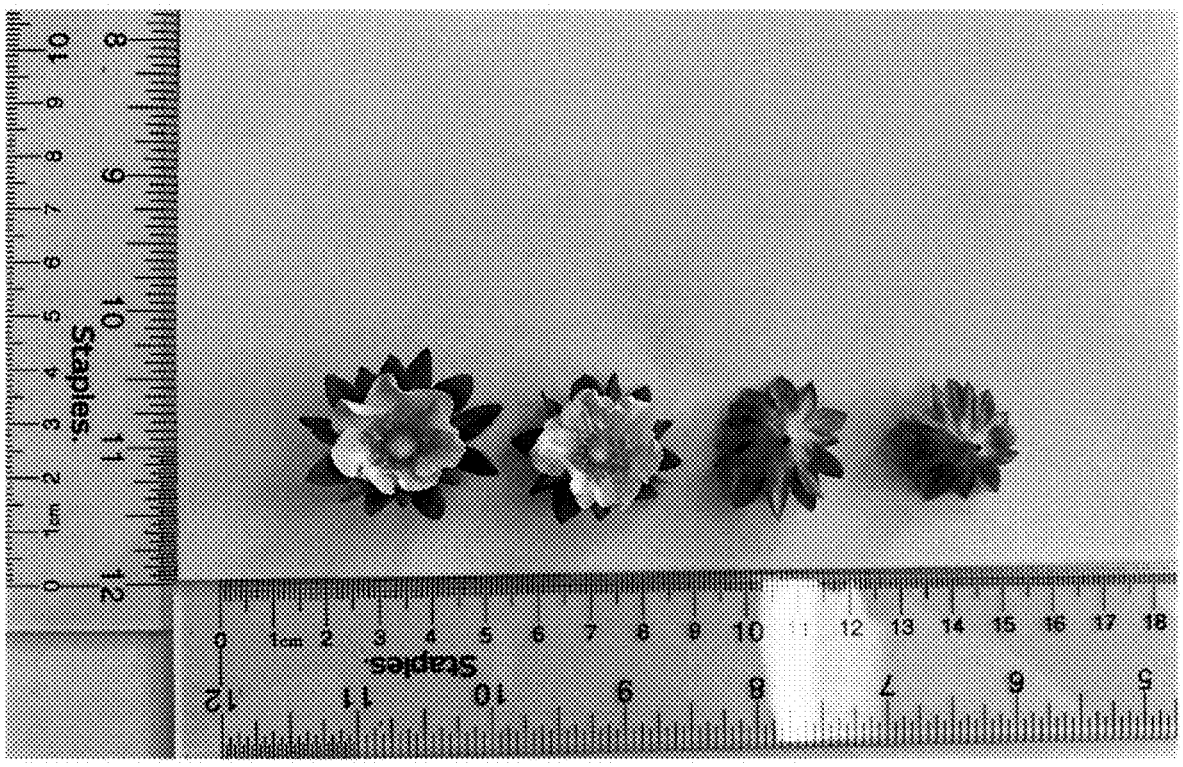
FIG. 9 shows several flowers of the new variety 'Plared 18009'.
Figure 10:
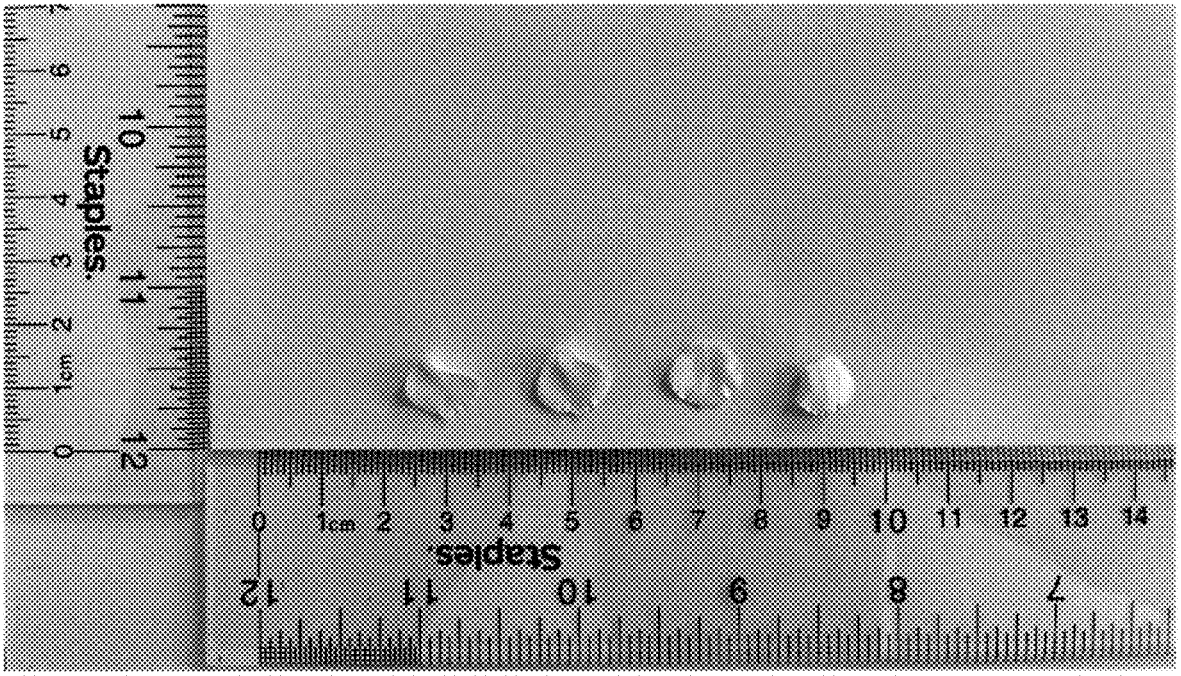
FIG. 10 shows several petals of the new variety 'Plared 18009': the upper side is represented by the two petals on the left, and the underside is represented by the two petals on the right.
Figure 11:
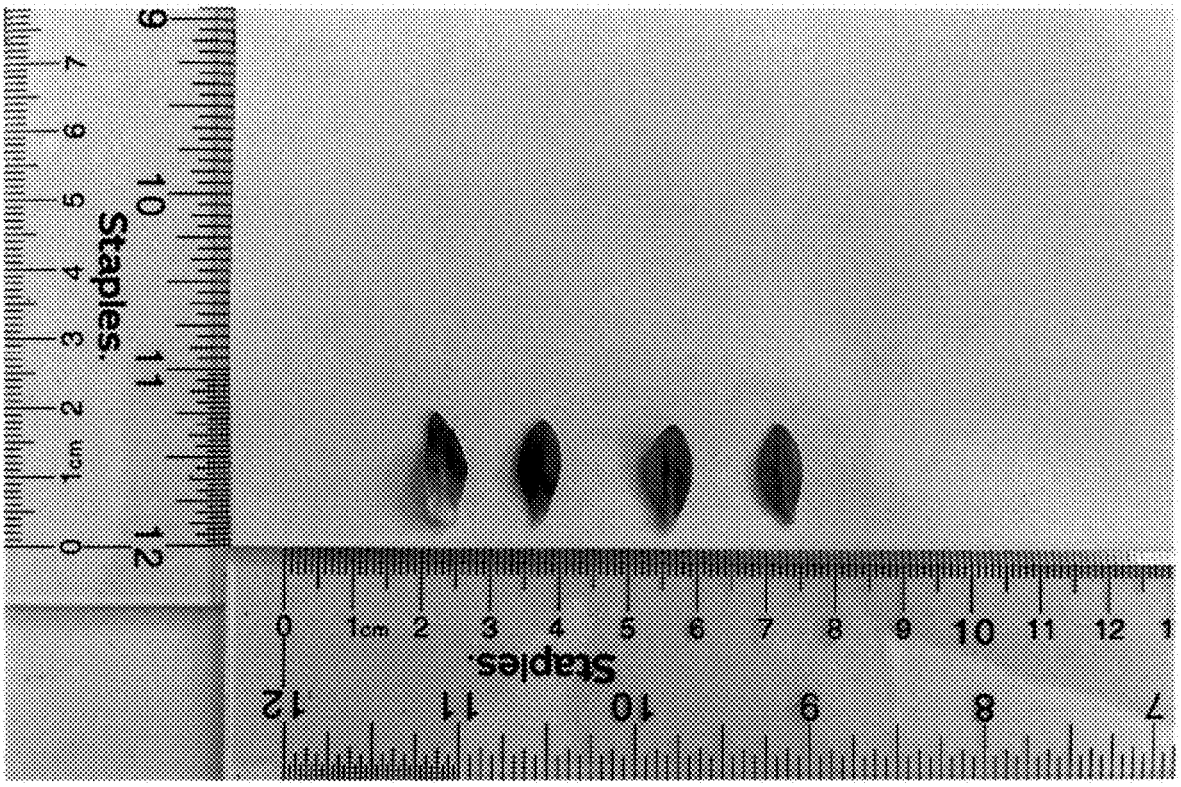
FIG. 11 shows the upper side and underside of typical sepals of the new variety 'Plared 18009'. The upper side is represented by the two sepals on the left, RHS Green near 139 B to 139 A, and the underside is represented by the two sepals on the right, RHS Green near 143 B to 143 A.
Figure 12:
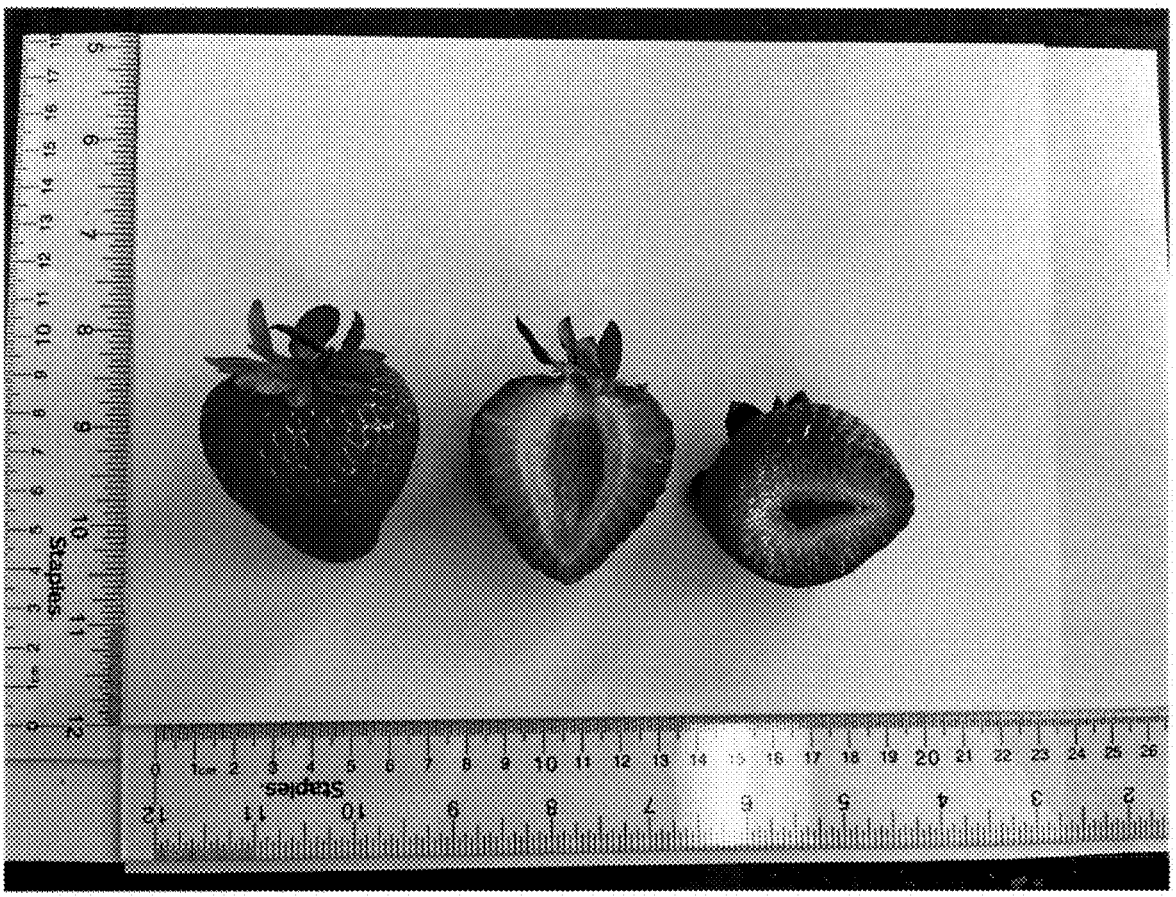
FIG. 12 shows typical fruit of the new variety whole, sliced and in cross section, illustrating the typical Medium Orange-Red 34A fruit color, the typical Light Orange-Red 33C flesh coloration, and a Light Orange 27D or White core.
Figure 13:
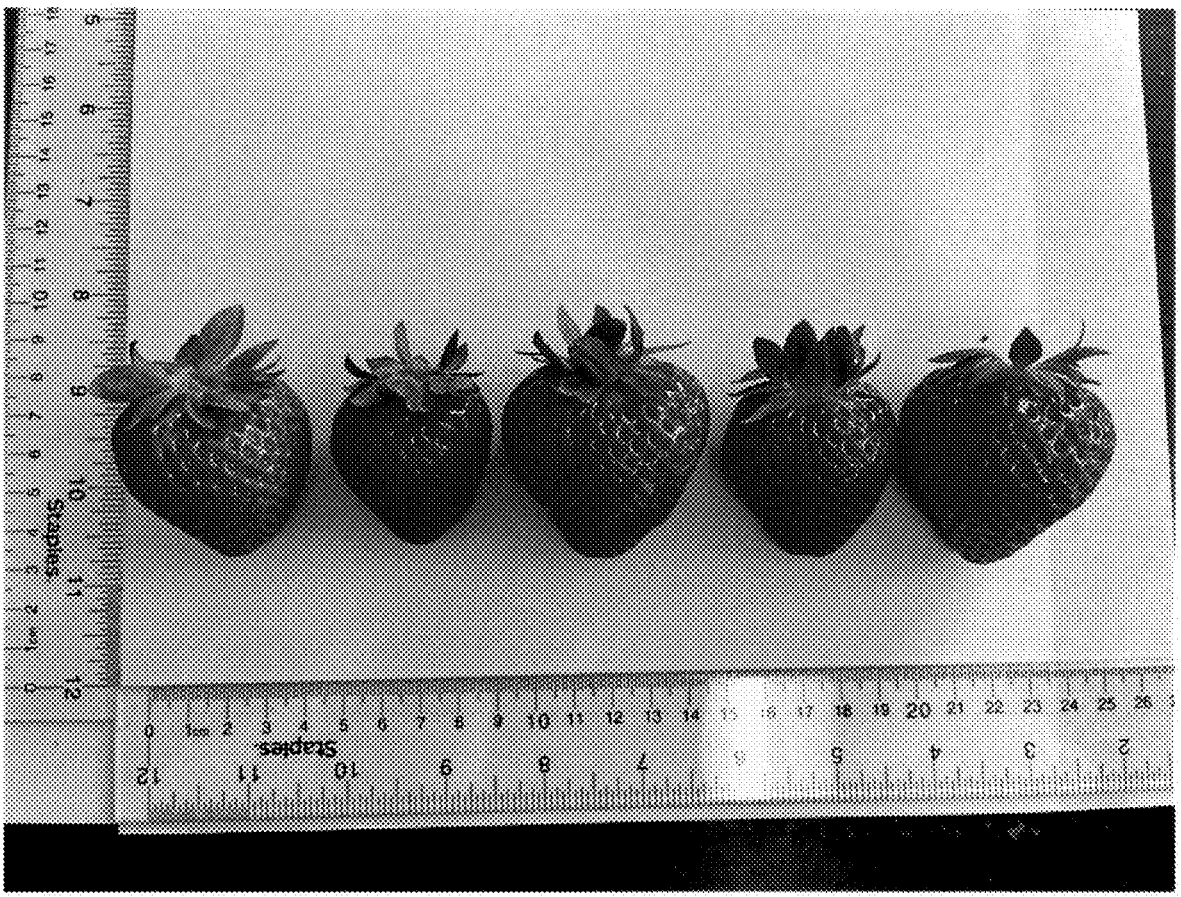
FIG. 13 shows several typical fruits of the new variety illustrating the typical conical shape and Medium Orange-Red 34A fruit color.
Figure 14:
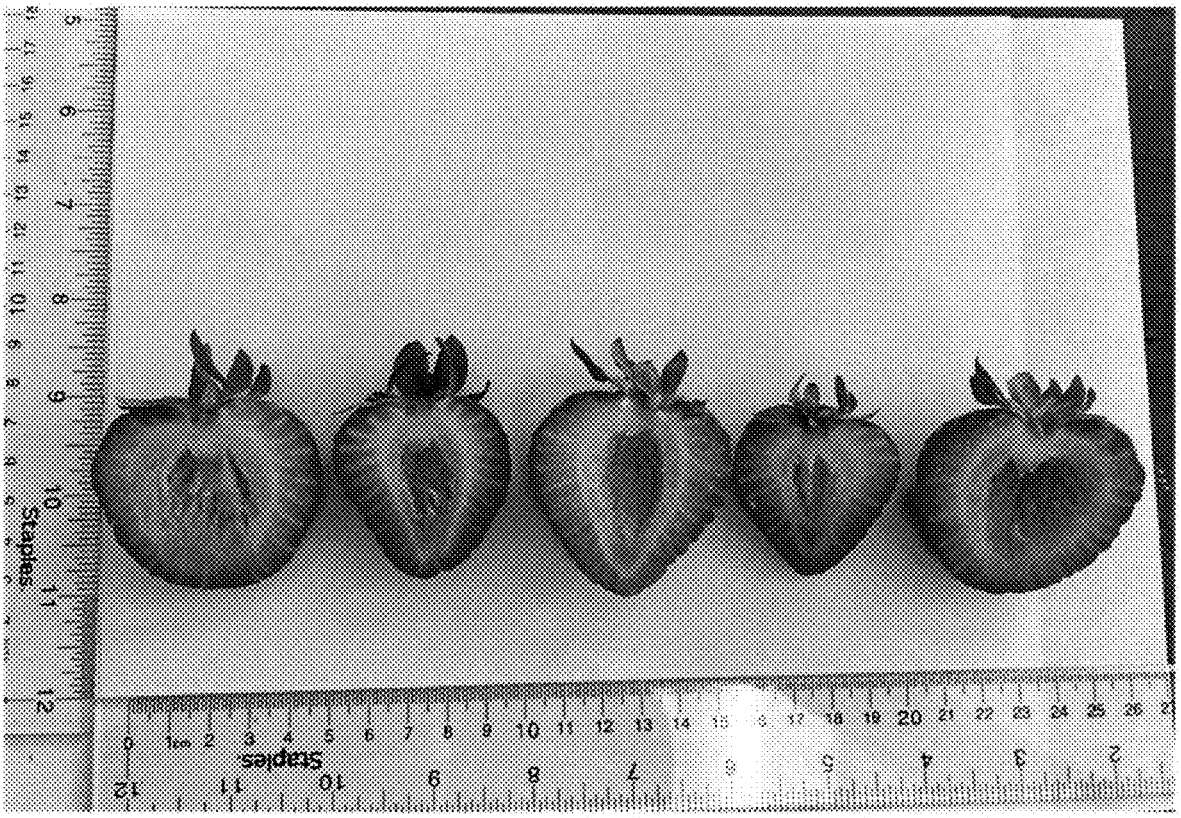
FIG. 14 shows several typical fruits of the new variety in cross section illustrating the typical Light Red coloration lightening toward the center, which is White with a Light Orange 27D hue.
Figure 15:
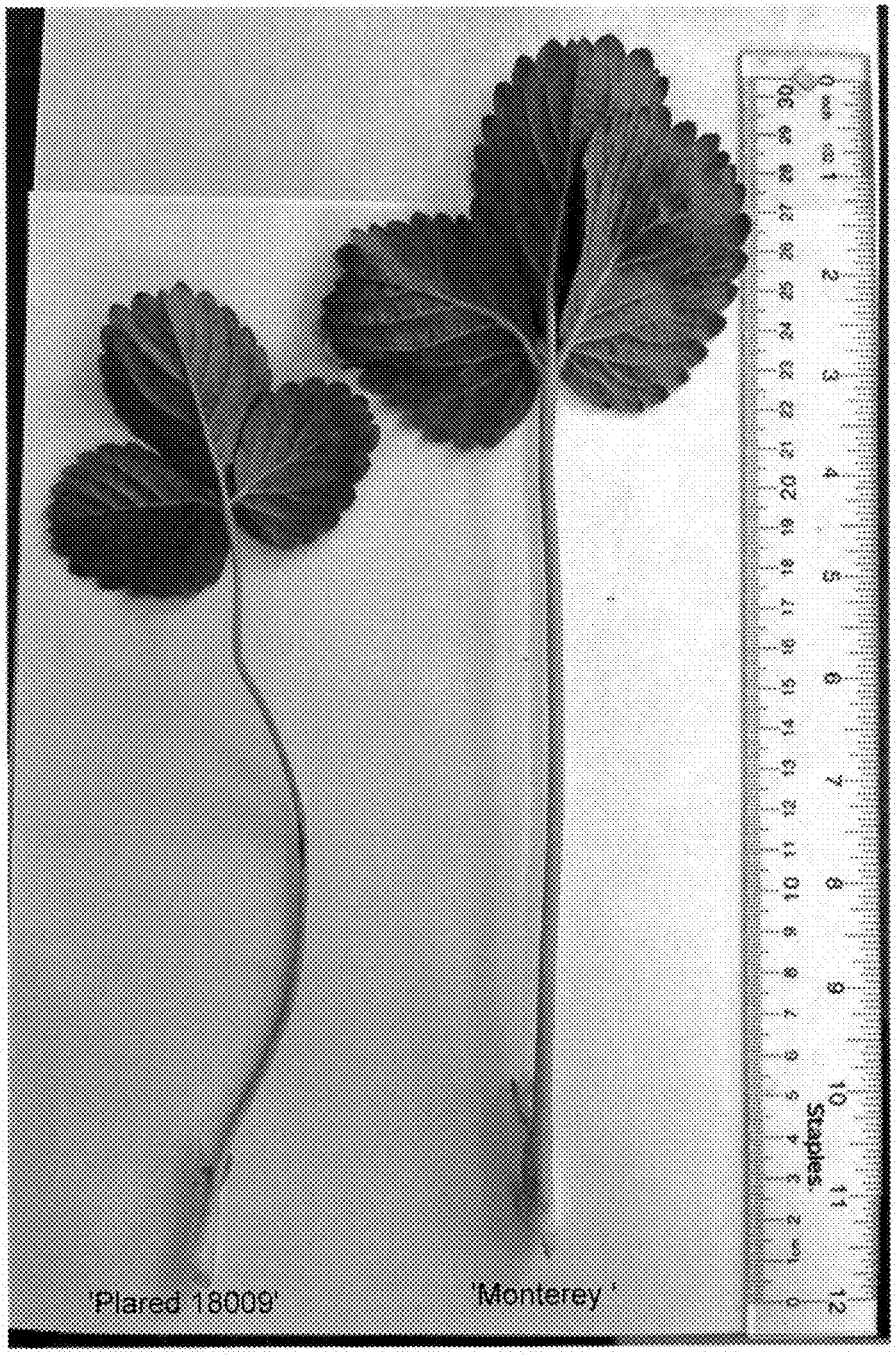
FIG. 15 shows the lower side of a complete leaf of the new variety 'Plared 18009' with Light Green 142D color and a serrate to crenate terminal leaflet margin, in comparison with the lower side of a complete leaf of strawberry variety 'Monterey', with Light Green 142D color near and a serrate to crenate terminal leaflet margin.
Figure 16:
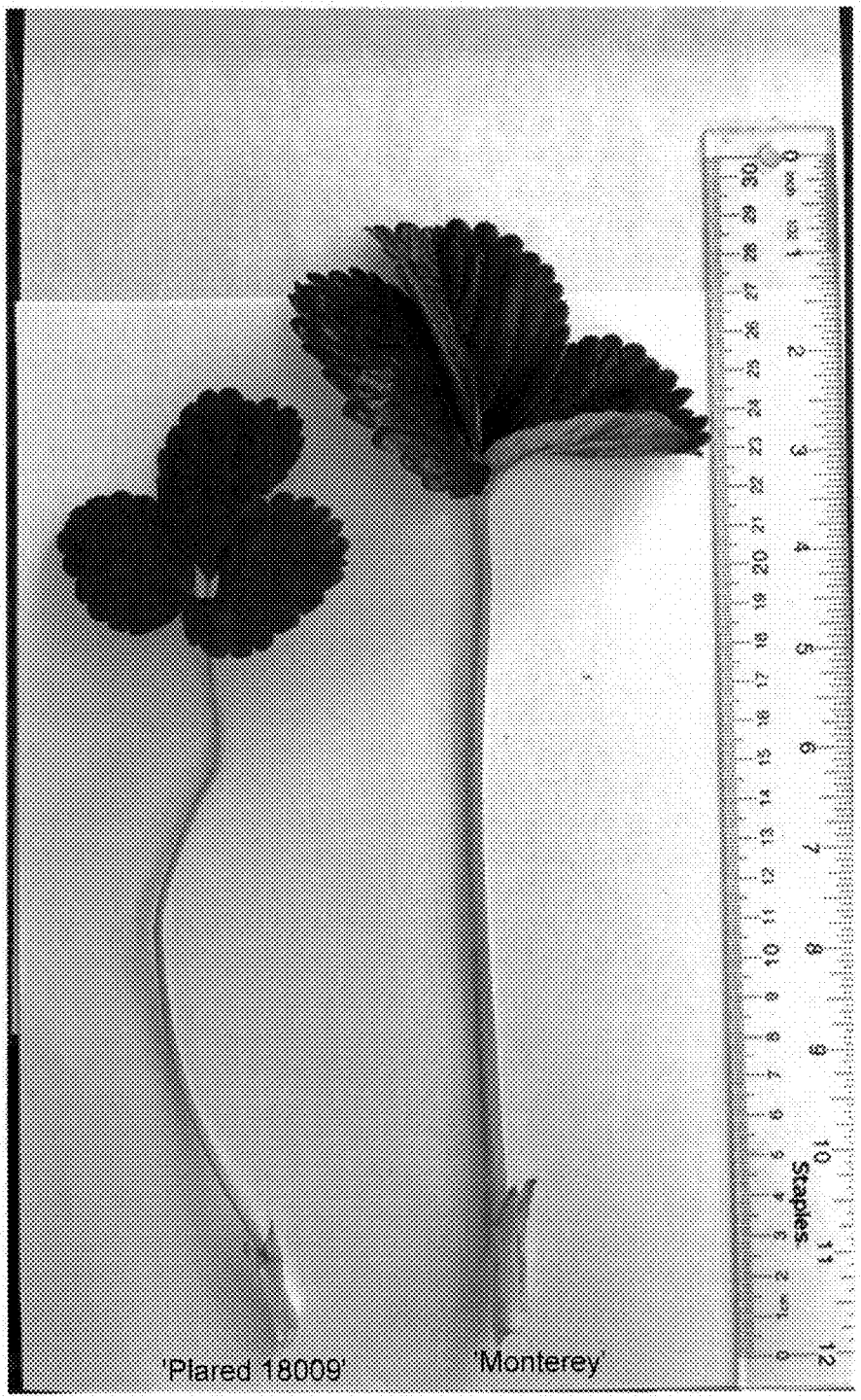
Figure 17:
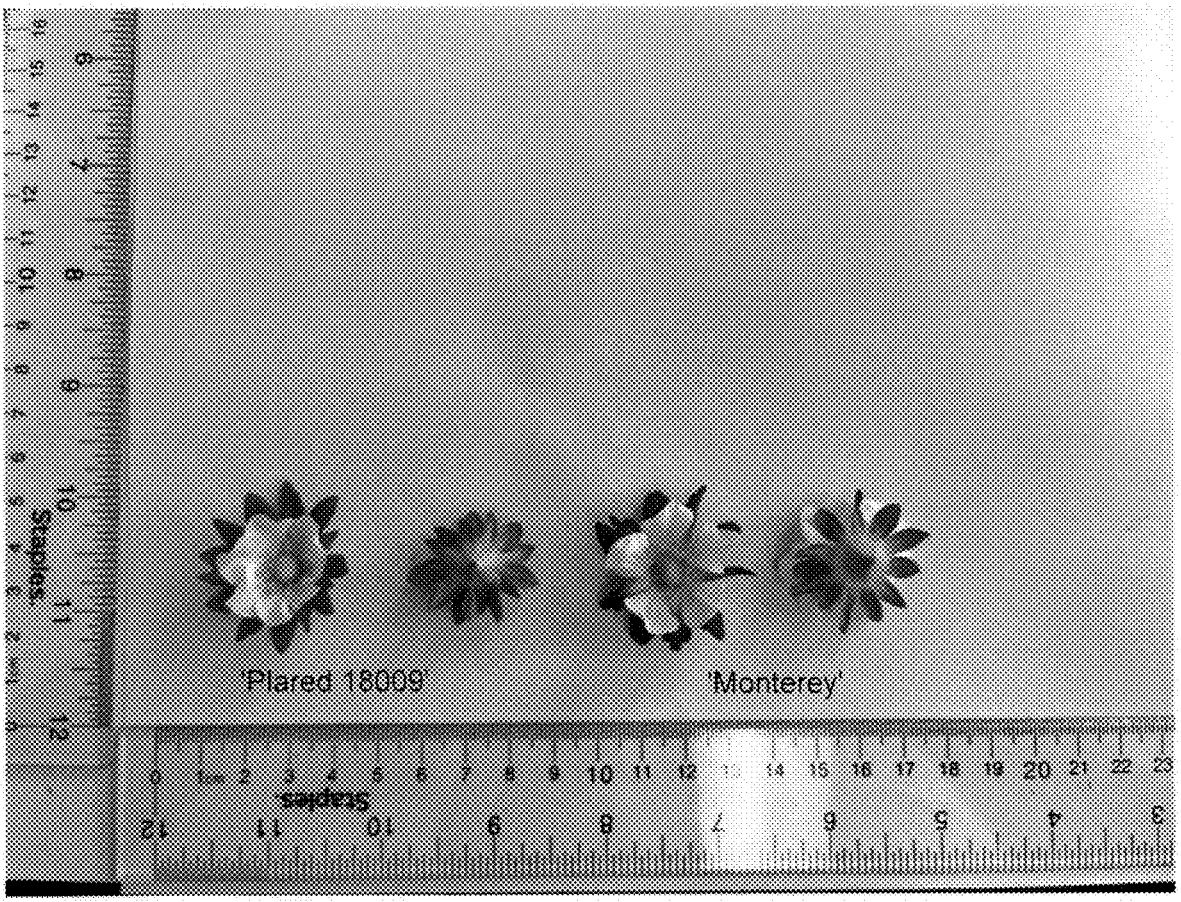

FIG. 16 shows the upper side of a complete leaf of the new variety 'Plared 18009' with Light Green 142A color near and a serrate to crenate terminal leaflet margin, in comparison with the upper side of a complete leaf of strawberry variety 'Monterey', with Dark Green 143A color near and a serrate to crenate terminal leaflet margin FIG. 17 shows a comparison between flowers of the new variety 'Plared 18009' and the strawberry variety 'Monterey'. The flower of 'Monterey' shows the ¾ size ratio of the calyx (3.75 cm) to the corolla (3.0 cm), whereas the flower of new variety shows a ¾ size ratio of the calyx (3.5 cm) to the corolla (2.0 cm).

Figure 18:
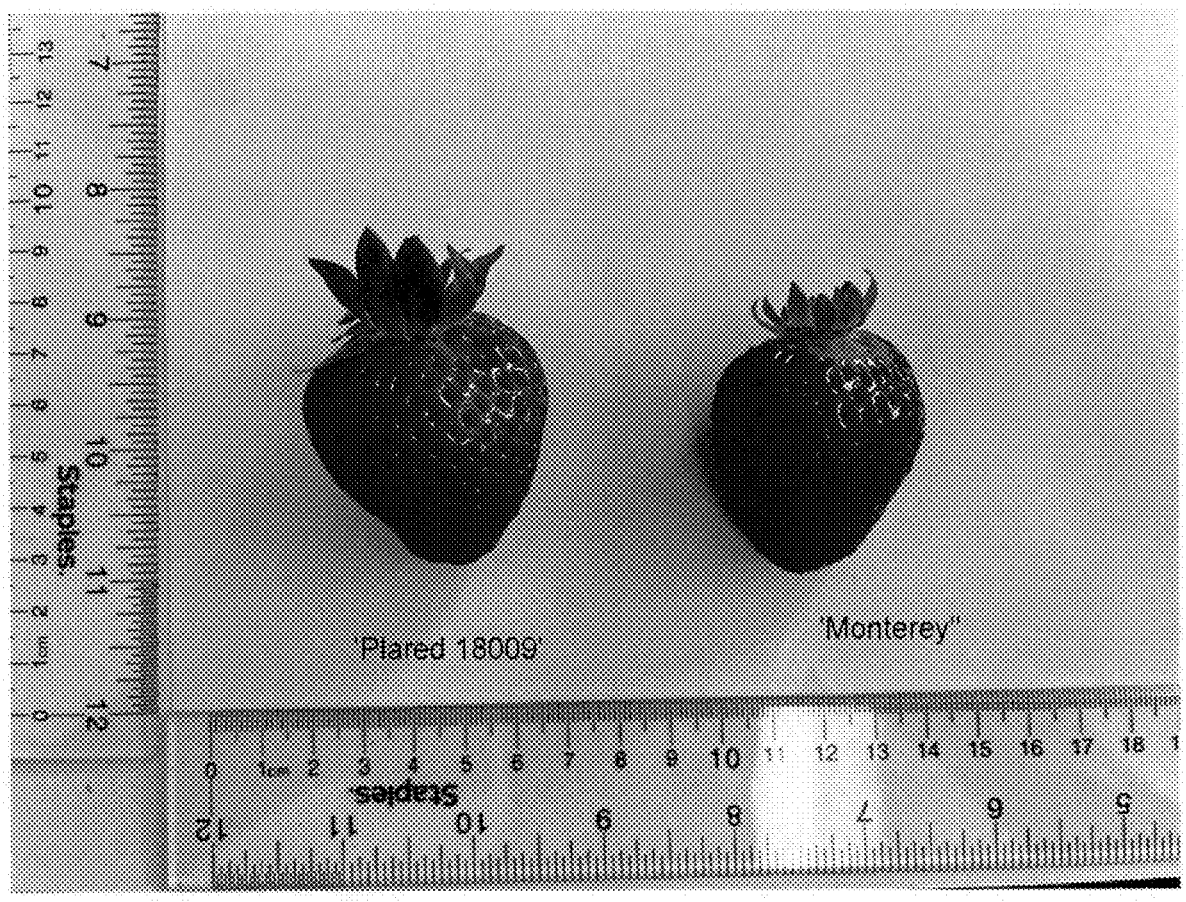

FIG. 18 shows a comparison between whole fruits of the new variety 'Plared 18009' and the strawberry variety 'Monterey'. The fruit of 'Monterey' has a 27.6-gram average fruit size, a medium band without achenes, and an outwards attitude of sepals whereas the fruit of the new variety has a 27.7-gram average fruit size, with a narrow band without achenes and the attitude of the sepals is outwards and downwards.

Figure 19:
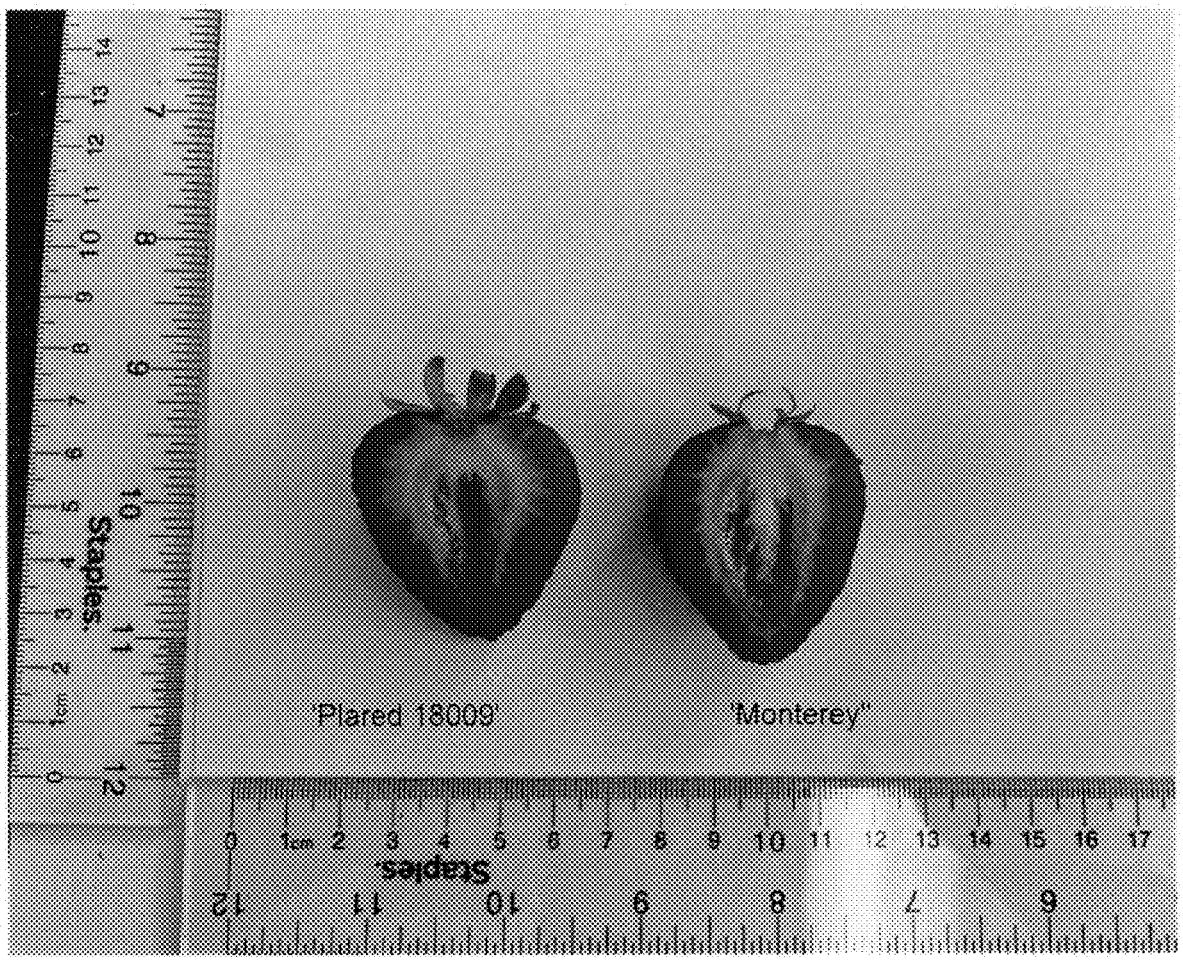

FIG. 19 shows a comparison of the fruit in cross section of the new variety 'Plared 18009' and the fruit in cross section of the strawberry variety 'Monterey'. The position of the calyx attachment is inserted with the fruit on both the new variety and 'Monterey'.

Figure 20:
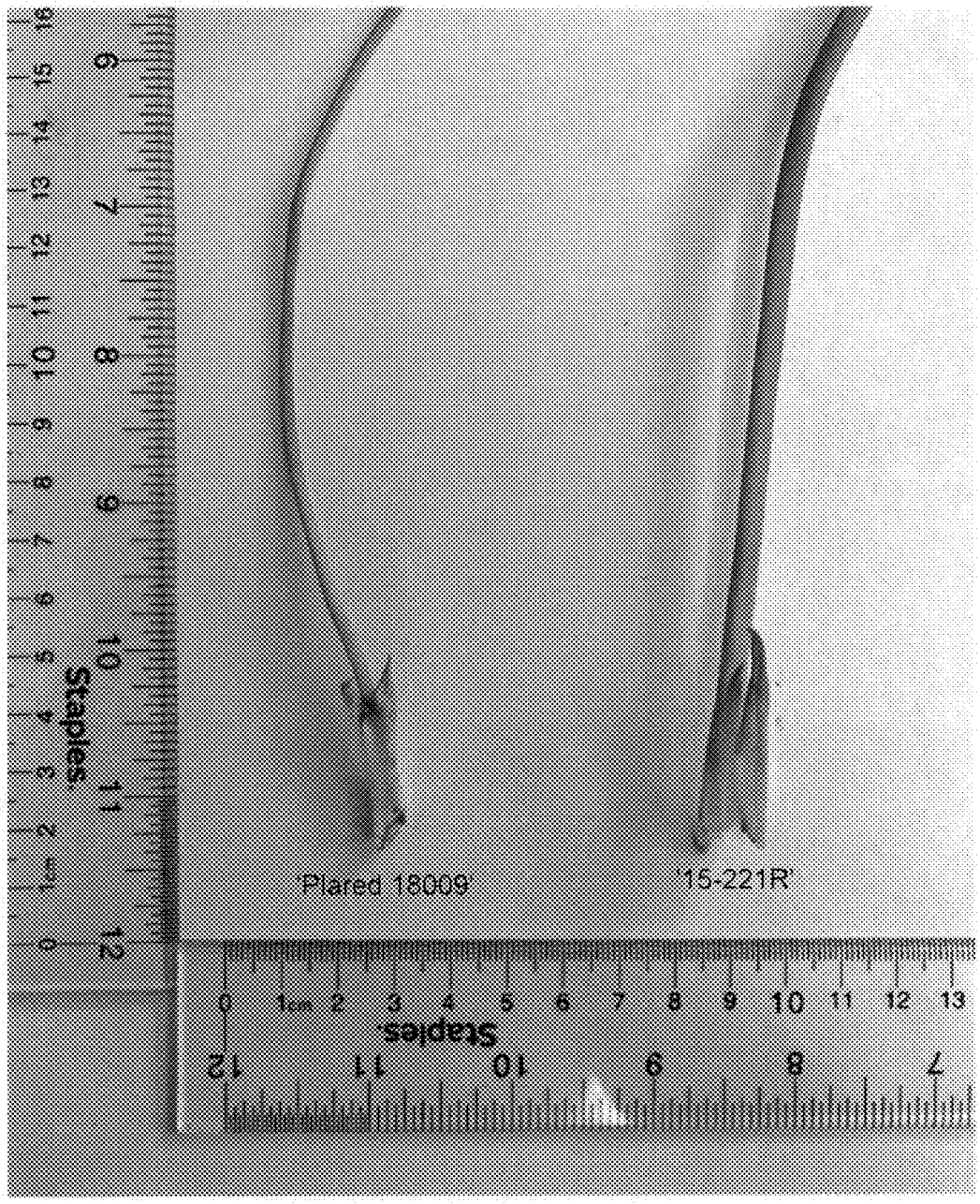

FIG. 20 shows the new variety 'Plared 18009' with a smaller, Light Green colored stipule measuring 3.3 cm in length and a thinner petiole 3 mm in diameter, in comparison with the pollen parent '15-221R', with a larger, medium green to Light Yellow-Green 145C stipule measuring 4.3 cm in length and a thicker petiole 5 mm in diameter. Both varieties show weak anthocyanin expression in the stipules color Medium Red-Purple 58B.

Figure 21:
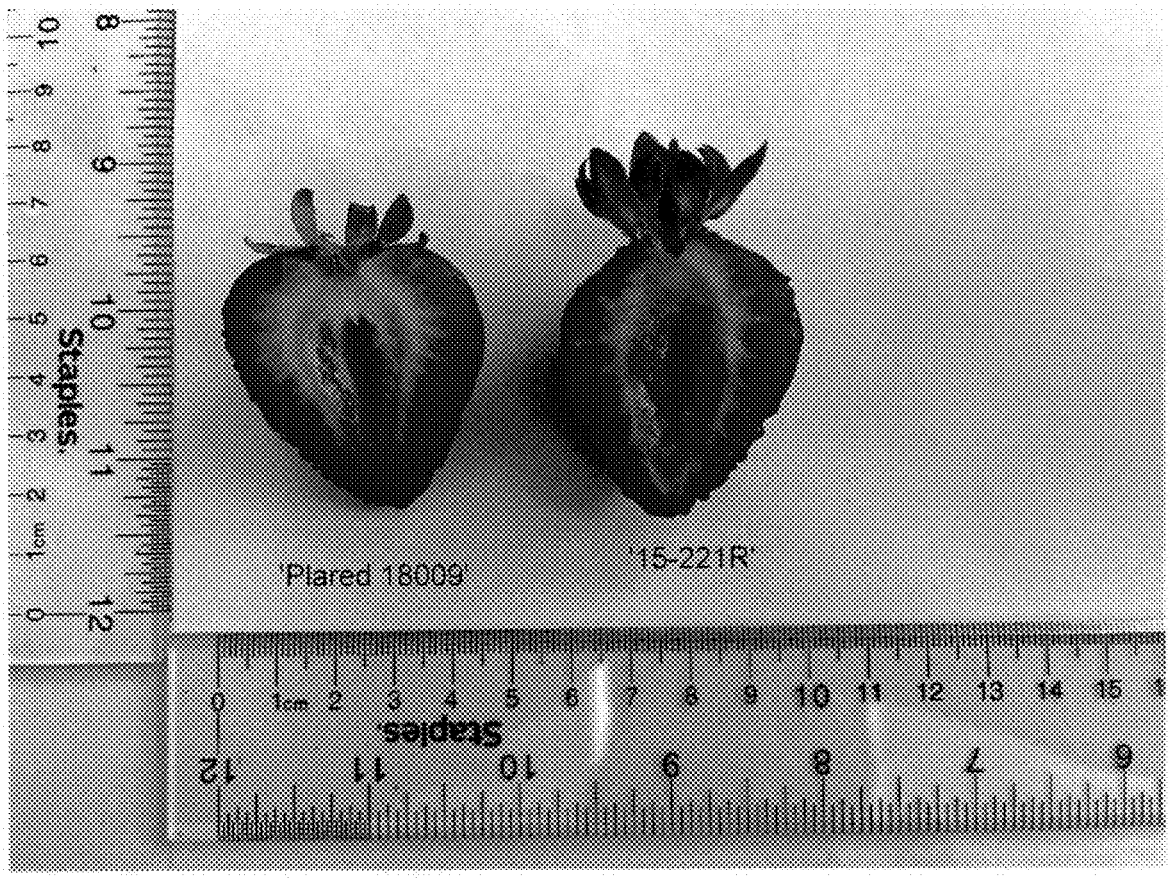

FIG. 21 shows a comparison of the fruit in cross section of the new variety 'Plared 18009' and the fruit in cross section of the pollen parent '15-221R'. The position of the calyx attachment is inserted in the fruit of the variety '15-221R', as it is in the fruit of the new variety 'Plared 18009'. The fruit shape differs between the new variety and the pollen parent, with the new variety being clearly conical and the pollen parent being slightly biconical.

Figure 22:
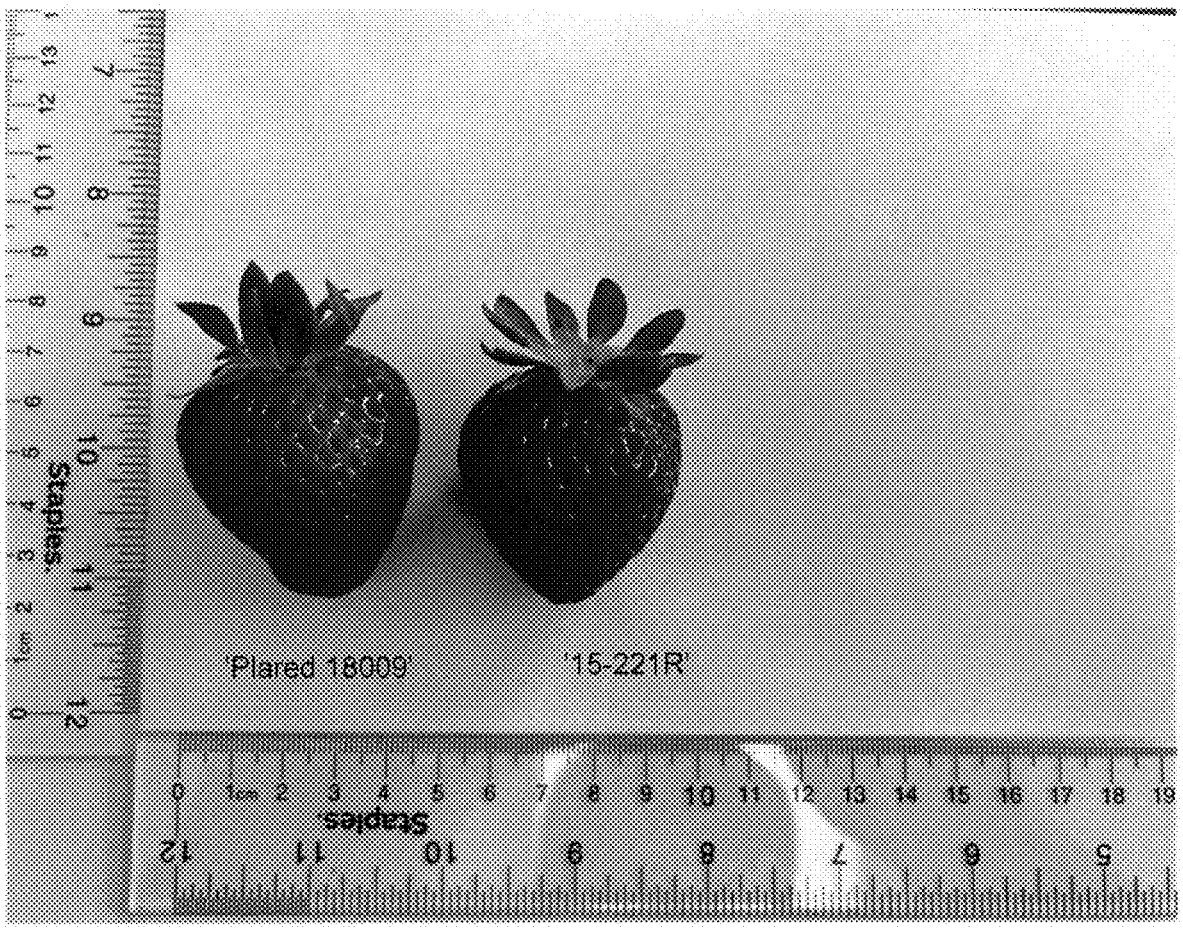

FIG. 22 shows a comparison between whole fruits of the new variety 'Plared 18009' and the strawberry variety '15-221R'. The pollen parent '15-221R' has Dark Red 42A fruit, a 24.3-gram average fruit weight, a medium band without achenes, and an outward attitude of sepals, whereas the new variety has larger Medium Orange-Red 34A colored fruit, a 27.7-gram average fruit weight, a narrow band without achenes and the attitude of the sepals is outwards and downwards.

Figure 23:
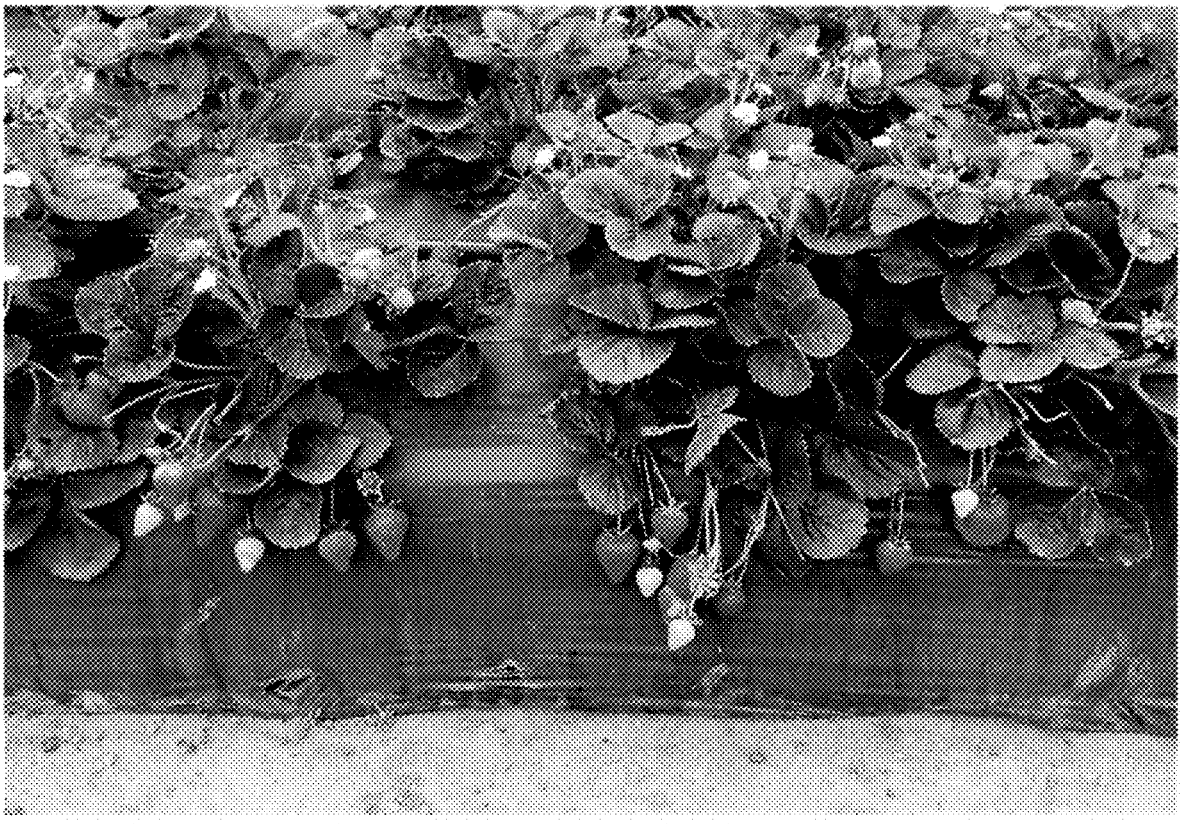

FIG. 23 shows several plants of the seed parent '16-69R'.

Figure 24:
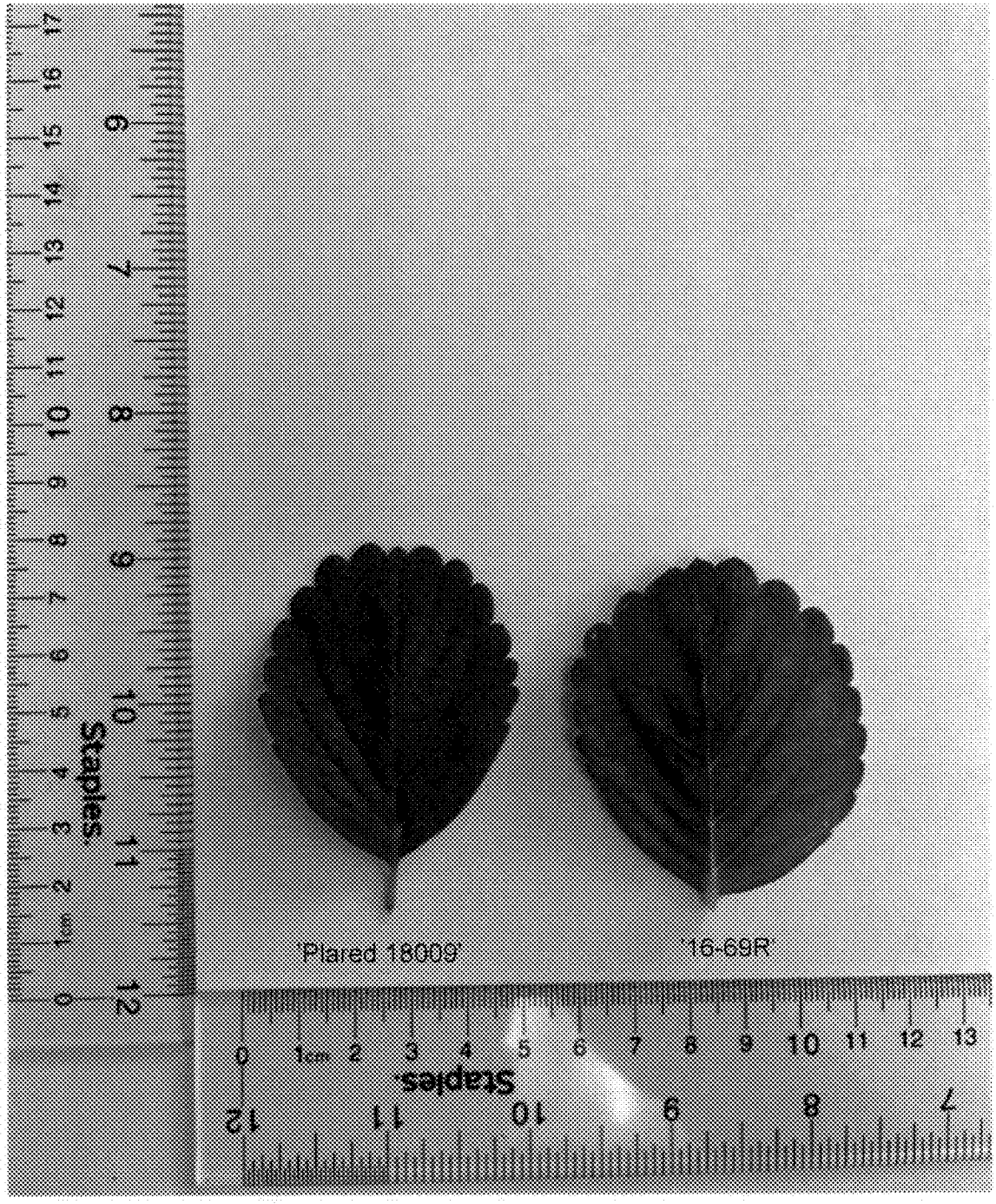

FIG. 24 shows the upper side of the terminal leaflet of 'Plared 18009' and the seed parent '16 69R'. The terminal leaflet of 'Plared 18009' is more elongated than that of '16-69R'. Also, there is a notable difference in color, with 'Plared 18009' having Light Green 142A coloring and '16-69R' having Dark Green 143A coloring.

Figure 25:
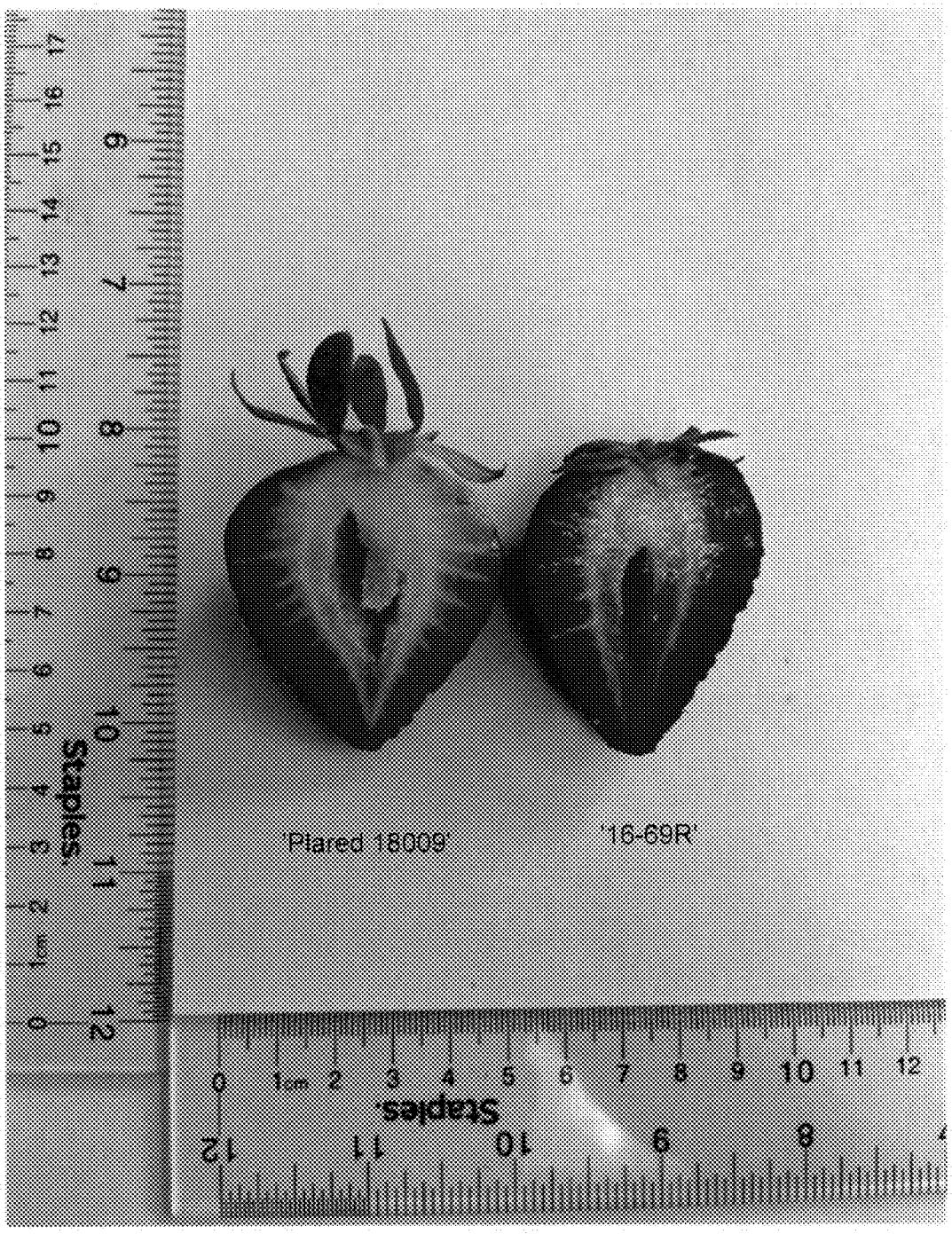

FIG. 25 shows a comparison of the fruit in cross section of the new variety 'Plared 18009' and the fruit of the pollen parent '16-69R'. The position of the calyx attachment is inserted for the fruit of both varieties.

Figure 26:
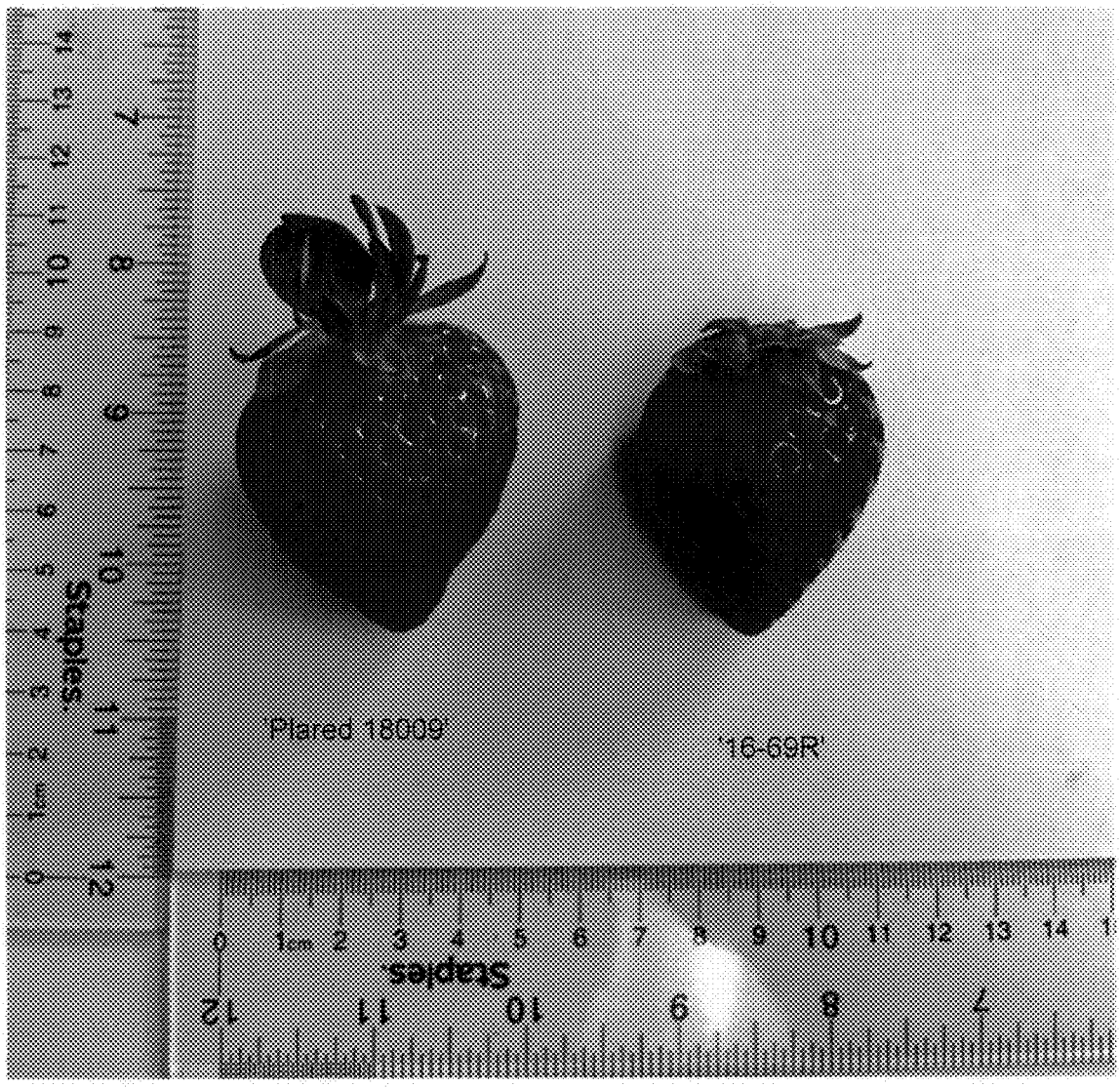

FIG. 26 shows a comparison between whole fruits of the new variety 'Plared 18009' and the seed parent variety '16-69R'. The seed parent '16-69R' has an average fruit size of 25.5-grams, a narrow band without achenes, and an attitude of the sepats which is inward, whereas the new variety has an average fruit weight of 27.7-grams, with a narrow band without achenes and the attitude of the sepals is outwards and downwards.

DESCRIPTION OF THE NEW VARIETY

The following detailed description of the new variety 'Plared 18009' is based upon observations taken of plants and fruits grown in Watsonville, California from 2018-2022. The sample size of plants was one in 2018, 10 in 2019, 40 in 2020, 100 in 2021 and 400 in 2022. Similar observations are expected to apply to plants grown under similar conditions of soil and climate. The colors are in accordance with The Royal Horticultural Society Colour Chart, London England, except where general color terms are used.

DETAILED DESCRIPTION

The following additional information is provided to further describe the new variety.

General:
- *Time of beginning of flowering*.—Early, about December 13$^{th}$.
- *Time of beginning of ripening*.—Early, about January 24$^{th}$.

Plant:
- *Habit*.—Semi-upright.
- *Density*.—Medium.
- *Vigor*.—Medium.
- *Height*.—Short, approximately 15 cm to 30 cm.
- *Width*.—Medium, approximately 20 cm to 40 cm.
- *Position of inflorescence in relation to foliage*.—Slightly above.
- *Number of stolons*.—Few. Stolon anthocyanin coloration: Weak to medium. Stolon density of pubescence: Sparse.

Leaf:
- *Upperside color*.—About Light Green 142A.
- *Underside color*.—About Light Green 142D.
- *Size*.—Medium. Length: Medium, approximately 9 cm. Width: Medium, approximately 12 cm.
- *Shape in cross section*.—Some leaves appear straight, and others appear concave.
- *Leaf surface undulation or blistering*.—Medium.
- *Leaf stem diameter*.—Approximately 3 mm to 5 mm.
- *Number of leaflets*.—Three only.
- *Variegation*.—Absent.
- *Glossiness*.—Medium.

Leaf stem characteristics:
- *Color*.—About Light Yellow-Green 145C.
- *Position of hairs*.—Horizontal.
- *Length*.—Medium, approximately 10 cm.

Terminal leaflet:
- *Length/width ratio*.—6:5.
- *Length*.—Medium, approximately 6 cm.
- *Width*.—Medium, approximately 5 cm.
- *Shape in cross section*.—Some leaves appear straight and others appear concave.
- *Shape of base*.—Obtuse.
- *Margin*.—Serrate to crenate.

Petiole:
- *Attitude of hairs*.—Slightly outwards.
- *Length*.—Small, about 0.5 cm.
- *Diameter*.—Approximately 3 mm.
- *Color*.—About Light Yellowish green 145C.

Stipule:
- *Anthocyanin coloration*.—Weak.
- *Length*.—Approximately 3.3 cm.
- *Color*.—About Light Yellow-Green 145C with weak anthocyanin coloration that is strong Medium Red-Purple 58B.

Stolons:
- *Length*.—Medium, approximately 45 cm.
- *Thickness*.—Thin, approximately 0.2 cm.
- *Pubescence density*.—Sparse.
- *Color*.—About Light Yellow-Green 144D with strong Medium Red-Purple 58B anthocyanin coloration.
- *Anthocyanin coloration*.—Present.

Inflorescence:
- *Position relative to foliage*.—Slightly above.
- *Number of flowers*.—Medium, the number will depend on growth stage.

Pedicel:
- *Position of hairs*.—Slightly outwards.
- *Average length*.—Approximately 9.2 cm.
- *Average diameter*.—Approximately 2.3 mm.
- *Color*.—About Light Yellow-Green 145C.

Flower:
- *Diameter*.—Medium.
- *Size of calyx relative to corolla*.—Larger.
- *Arrangement of petals*.—Overlapping.
- *Diameter primary flowers*.—Medium, approximately 3 cm.
- *Diameter secondary flowers*.—Medium, approximately 2 cm.
- *Number of petals*.—6.
- *Fragrance*.—Weakly floral.
- *Time from bloom to mature fruit*.—About 28 days.
- *Stamens*.—Present. Length: Approximately 3 mm. Color: About Medium Yellow 12B. Average number: Approximately 26.
- *Anthers size*.—Medium.
- *Color*.—About Medium Yellow 12B.
- *Pollen*.—Medium. Color: About Medium Yellow 12B.

*Pistils*.—Size: Medium, approximately 2 mm. Color: About Medium Yellow 5A.

Petal:

*Length/width ratio*.—Equal.

*Length*.—Medium, approximately 1 cm.

*Width*.—Medium, approximately 1 cm.

*Shape*.—Circle to slight oval. When oval there is slightly more width than length.

*Color*.—About White 155D.

*Shape of base*.—Rounded.

*Shape of apex*.—Rounded.

*Shape of margin*.—Rounded.

*Texture*.—Absent to weak blistering.

Sepal:

*Calyx*.—Presents 10 to 14 sepals with ellipse shape.

*Attitude of sepals*.—Outwards to downwards.

*Color upperside of sepals*.—About Medium Green 134A.

*Color underside of sepals*.—About Light Green 138B.

*Length of sepals*.—Medium, approximately 20 mm.

*Width of sepals*.—Medium, approximately 7.5 mm.

Fruit:

*Ratio of length/maximum width*.—Moderately longer.

*Color*.—About Dark Orange-Red 34A

*Length*.—Long, approximately 5.5 cm.

*Width*.—Medium, approximately 5 cm.

*Size*.—Large.

*Shape*.—Conical.

*Difference in shapes between primary and secondary fruits*.—Slight.

*Band without achenes*.—Narrow.

*Evenness of surface*.—Even or slightly uneven.

*Evenness of color*.—Even or very slightly uneven

*Glossiness*.—Medium.

*Position of achenes*.—Below surface.

*Insertion of calyx*.—Inserted.

*Size of calyx in relation to fruit diameter*.—Slightly smaller.

*Adherence of calyx*.—Strong.

*Firmness*.—Medium.

*Color of flesh*.—About Medium Orange-Red 33C.

*Distribution of orange red color of flesh*.—Even distribution except for the core which is Light Orange 27D.

*Hollow center*.—Expressed.

*Color of core*.—White with a slight Light Orange 27D.

*Sweetness*.—Medium.

*Acidity*.—Medium.

*Time of flowering* (50% *of plants at first flower*).—Early, January 3$^{rd}$.

*Time of ripening* (50% *of plants with ripe fruits*).—Early, January 24$^{th}$.

*Type of bearing*.—Day neutral.

*Production peaks* (*continuous production*).—Peak 1: Week of January 24$^{th}$, producing approximately 147.5 g of marketable fruit per plant. Peak 2: Week of May 23$^{rd}$, producing approximately 1569.9 g of marketable fruit per plant. Peak 3: Week of June 27$^{th}$, producing approximately 829.4 g of marketable fruit per plant. Peak 4: Week of August 1$^{st}$, producing approximately 288.7 g of marketable fruit per plant.

*Chilling*.—Approximately 400 to 600 hours.

*Cavity*.—Medium to large.

Storage qualities: The new variety 'Flared 18009' post-harvest life is slightly better, since the light fruit color naturally counterbalances the darkening that occurs during storage. The fruit of the new variety 'Flared 18009' will last an average of 7 to 10 days if shaded immediately after harvest and placed in a forced air cooler within two hours after harvest.

Disease resistance: The new variety 'Flared 18009' has shown strong resistance to *Fusarium oxysporum*.

Market use: The fruit of the new variety 'Plared 18009' is primary sold primarily as fresh fruit. However, it is also occasionally sold into the freezer market or the juice market.

We claim:

1. A new and distinct variety of strawberry plant named 'Plared 18009' as herein described and illustrated.

* * * * *

FIGIRE 18